United States Patent [19]

Meguro et al.

[11] Patent Number: 5,223,513
[45] Date of Patent: Jun. 29, 1993

[54] QUINOLINE DERIVATIVES, THEIR PRODUCTION AND USE

[75] Inventors: Kanji Meguro, Nishinomiya; Hitoshi Ikeda, Higashiosaka, both of Japan

[73] Assignee: Takeda Chemical Industries, Ltd., Osaka, Japan

[21] Appl. No.: 587,795

[22] Filed: Sep. 25, 1990

[30] Foreign Application Priority Data

Oct. 6, 1989 [JP] Japan .................................. 1-262782
Dec. 11, 1989 [JP] Japan .................................. 1-322290

[51] Int. Cl.⁵ ..................... A61K 31/55; C07D 215/20
[52] U.S. Cl. .................................... 514/312; 546/157; 546/163; 514/313
[58] Field of Search ................ 546/157, 163; 514/312, 514/313

[56] References Cited

U.S. PATENT DOCUMENTS

| | | | |
|---|---|---|---|
| 3,514,459 | 5/1970 | Ritler | 546/157 |
| 3,798,226 | 3/1974 | Meguro et al. | |
| 3,862,152 | 1/1975 | Kuwada et al. | |
| 4,530,931 | 7/1985 | Musser et al. | 546/157 X |
| 4,684,645 | 8/1987 | Chang et al. | 546/157 X |

Primary Examiner—Marianne M. Cintins
Assistant Examiner—Catherine S. Kilby Scalzo
Attorney, Agent, or Firm—Wegner, Cantor, Mueller & Player

[57] ABSTRACT

A quinoline derivative of the formula (I):

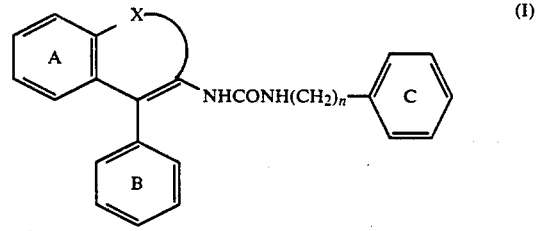

wherein each phenyl ring of A, B and C can have one or more substituents, X is

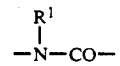

($R^1$ is a hydrogen atom or a lower alkyl group) or

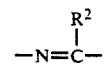

($R^2$ is a lower alkyl group or a lower alkoxy group), and n is 0 or 1, or its salt, which possesses an inhibitory action against acyl-CoA: cholesterol acyltransferase.

24 Claims, No Drawings

QUINOLINE DERIVATIVES, THEIR PRODUCTION AND USE

BACKGROUND OF THE INVENTION

1. Field of the Invention

This invention relates to novel quinoline derivatives, their production and use. The compounds of this invention possess excellent inhibitory action against acyl-CoA : cholesterol acyltransferase (ACAT). Especially, the compounds of this invention inhibit the absorption of cholesterol through the intestinal tract of a mammal and also restrain the accumulation of cholesterol ester at the arterial wall, and accordingly are useful as a drug for preventing and treating hypercholesterolemia, atherosclerosis and various diseases caused thereby (e.g., ischemic cardiac diseases such as myocardial infarction, cerebrovascular disturbance such as cerebral infarction, cerebral apoplexy, etc.).

U.S. Pat. No. 3,862,152 mentions specifically 6-chloro-4-phenyl-3-(3-phenylureido)quinoline (Compound A), 6-chloro-3-[3-(4-chlorophenyl)ureido]-4-phenylquinoline (Compound B) and 3-(3-benzylureido)-6,7-dimethoxy-4-phenylquinoline (Compound C), which possess antiulcer action.

Also, 6-chloro-3-phenyl(or p-chlorophenyl) acetamido-4-phenylquinoline is known to be effective as an antitrichomonas or antiulcer agent (see U.S. Pat. No. 3,798,226).

There has not been any report that the above mentioned compounds possess pharmacological activity useful as a drug for arteriosclerosis such as ACAT inhibitory activity and blood cholesterol lowering activity, and these points have not been studied so far.

Therefore, it has not been known that the compounds A, B and C and their analogue compounds are useful as a drug for atherosclerosis.

SUMMARY OF THE INVENTION

The inventors of this invention studied the physiological activities of the above mentioned compounds A, B and C and their analogue compounds, and found that new compounds having oxo, alkyl or alkoxy group at 2-position, which are not described concretely in the above mentioned publications, possess potent ACAT inhibitory activity and are useful as a drug for atherosclerosis.

Thus, this invention relates to (1) a quinoline derivative of the formula (I):

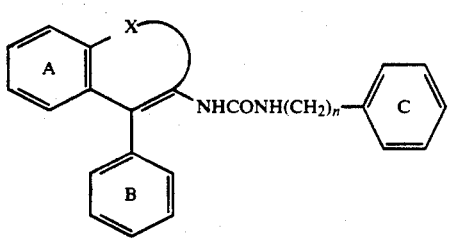

wherein each phenyl ring of A, B and C can have one or more substituents, X is

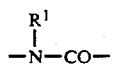

($R^1$ is a hydrogen atom or a lower alkyl group) or

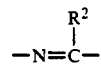

($R^2$ is a lower alkyl group or a lower alkoxy group), and n is 0 or 1, or its salt;

(2) an ACAT inhibitory composition comprising a quinoline derivative of the formula (I), or its salt;

(3) a method for the preparation of a quinoline derivative of the formula (I) and its salt.

DESCRIPTION OF THE PREFERRED EMBODIMENT

The symbol X of the formula (I) represents

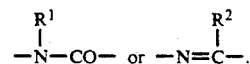

Preferably, the lower alkyl groups for $R^1$ and $R^2$ are straight or branched chain ones having 1–6 carbon atoms, such as methyl, ethyl, propyl, isopropyl, butyl, isobutyl, sec-butyl, tert-butyl, pentyl, isopentyl, neopentyl, hexyl and the like.

Preferably, the lower alkoxy groups for $R^2$ are straight or branched chain ones having 1–6 carbon atoms, such as methoxy, ethoxy, propoxy, isopropoxy, butoxy, isobutoxy, sec-butoxy, tert-butoxy, pentyloxy, isopentyloxy, neopentyloxy and hexyloxy.

The symbol n is 0 or 1, and preferably n is 0.

Each of the A, B and C rings can have one or more substituents. Examples of the substituents are a halogen atom, an optionally halogenated lower alkyl group, an optionally halogenated lower alkoxy group, an optionally halogenated lower alkylthio group, nitro group, an optionally esterified carboxy group, hydroxyl group, a $C_{1-4}$ acyloxy (e.g., formyloxy, acetoxy, propionyloxy, butyryloxy, 2-methylpropionyloxy, etc.) and a $C_{1-3}$ acyl group (e.g., formyl, acetyl, propionyl, etc.). The halogen atom in these groups may be a fluorine, chlorine, bromine or iodine atom.

The optionally halogenated lower alkyl groups include the above mentioned lower alkyl groups and these lower alkyl groups substituted with two to five halogen atoms, such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl or 5-trifluoromethylpentyl.

The optionally halogenated lower alkoxy groups and the optionally halogenated lower alkylthio groups can be those formed by the combination of the above mentioned lower alkyl groups or halogenated lower alkyl groups and an oxygen atom or a sulfur atom.

The optionally esterified carboxy groups may be a carboxyl group and carboxy groups esterified by an alkyl of 1–6 carbon atoms such as methyl, ethyl, propyl, isopropyl, butyl, isobutyl, sec-butyl, tert-butyl, pentyl or hexyl.

The substituent(s) on the rings A, B and C can be at any position of each ring, and these substituents may be the same or different, and the number of the substituent(s) may be 1 to 4. The suitable position(s) of the substituent(s) are 6-, 7- and/or 8- positions of the quinoline nucleus for the ring A, 2- position for the ring B, and 2-, 4- and/or 6-positions for the ring C.

The compounds of the formula (I) can form their salts with acids (e.g., inorganic acids such as hydrochloric acid, hydrobromic acid, sulfuric acid and phosphoric acid; organic acids such as methanesulfonic acid, benzenesulfonic acid, fumaric acid, maleic acid, citric acid and tartaric acid), especially in case where X is

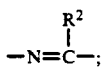

and also can form their salts with inorganic bases (e.g., sodium, potassium or calcium salt) in case where they contain an acid group such as carboxyl group. Preferably, these salts are pharmaceutically acceptable salts.

The quinoline derivative of the formula (I) and its salt can be prepared, for example, by reacting a compound of the formula (II):

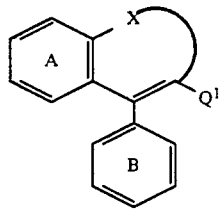

or its salt with a compound of the formula (III):

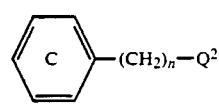

or its salt, wherein $Q^1$ and $Q^2$ are different and are $-NH_2$ or $-NCO$, and the other symbols have the same meanings as defined above.

The above mentioned compounds (II) and (III) wherein X is

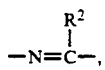

or $Q^1$ or $Q^2$ is $NH_2$ can form a salt thereof as mentioned before for the compound (I). The following description includes the compounds (I), (II) and (III) as well as their respective salts even if the compounds themselves are referred to.

The above method comprises reacting an amine with an isocyanate. When the compound (II) is an amine, the compound (III) in isocyanate form is reacted, and vice versa.

This reaction is usually carried out in an appropriate solvent. The solvents to be used may be any inert solvents, for example, ethers such as ethyl ether, diisopropyl ether, dimethoxyethane, tetrahydrofuran and dioxane; aromatic hydrocarbons such as benzene, toluene and xylene; esters such as methyl acetate and ethyl acetate; ketones such as acetone and methyl ethyl ketone; pyridine; N,N-dimethylformamide and the like. The reaction is usually carried out at about 0° C.–150° C., preferably at about 15° C.–120° C. The amount of the compound (II) or (III) wherein $Q^1$ or $Q^2$ is isocyanate is usually about 1–5 equivalents, preferably about 1–3 equivalents, to the compound (III) or (II) wherein $Q^2$ or $Q^1$ is amino. The reaction time is usually about 5–48 hours, preferably about 15 minutes–20 hours, although it varies with the kinds of the starting materials and solvents to be used, reaction temperature, etc.

Among the compounds (I) obtained in the above Methods, a compound having lower alkoxy group(s) in the ring A, B or C if required can be converted into a compound having hydroxyl group(s) by the reaction with boron tribromide or the like. This reaction is usually carried out in a solvent (e.g., dichloromethane, chloroform, carbon tetrabenzene, toluene, etc.), at about −20° C. -80° C., chloride, benzene, toluene, etc.), at about −20° C.-80° C., preferably at about 0° C.-30° C. The amount of boron tribromide to be used is about 1–10 equivalents, preferably about 1–5 equivalents, to each lower alkoxy group.

When the compound (I) prepared by the above method contains an esterified carboxy or acyloxy group in any of the rings A, B and C, such group if required can be converted into a carboxy or hydroxyl group, respectively, upon hydrolysis. The hydrolysis usually can be conducted by using an alkali metal or alkali earth metal hydroxide such as sodium hydroxide, potassium hydroxide or barium hydroxide in the presence of a solvent (e.g., an alcohol such as methanol, ethanol or propanol, or the like). The reaction temperature is about 0° C.–100° C., preferably about 20° C.-80° C.

The compound (I) which contains hydroxyl group(s) in the ring A, B and C if required can be converted into the corresponding one having alkoxy or acyloxy group(s) upon alkylation or acylation. The alkylation can be conducted by using an alkylating agent such as an optionally substituted alkyl halide (e.g., chloride, bromide or iodide) or an optionally substituted alkyl sulfate or sulfonate (e.g., dimethylsulfate, methanesulfonate, p-toluenesulfonate or benzenesulfonate) in a solvent (e.g., methanol, ethanol, propanol, dimethoxyethane, dioxane, tetrahydrofuran, acetone or dimethylformamide) in the presence of a base (e.g., potassium carbonate, sodium carbonate, potassium hydroxide or sodium hydroxide). The reaction temperature may be usually about −10° C.–100° C., preferably about 0° C.-80° C. The amount of the alkylating agent is about 1–2 equivalents, preferably about 1–1.5 equivalents, to the phenolic compound (I).

The acylation can be conducted by using an appropriate carboxylic acid or its reactive derivative. When the reactive derivative is used, the reaction is usually conducted in a solvent (e.g., benzene, toluene, ethyl ether, ethyl acetate, chloroform, dichloromethane, dioxane, tetrahydrofuran, N,N-dimethylformamide or pyridine), optionally in the presence of an appropriate base for accelerating the reaction (e.g., sodium hydrogen carbonate, potassium hydrogen carbonate, sodium carbonate, potassium carbonate, sodium acetate, triethylamine or pyridine). The reactive derivatives may be the acid anhydride, mixed acid anhydride or acid halide (e.g., chloride or bromide). The reaction temperature is usually about 0° C.–150° C., preferably about 10° C.–100° C.

The object compounds (I) obtained in the above methods can be isolated and purified by a known method for isolation and purification (e.g., condensation, extraction by solvent, column chromatography, recrystallization, etc.)

The compounds (I) possess excellent inhibitory action against acyl-CoA : cholesterol-acyltransferase (ACAT), and their acute toxicity and toxicity by repeated administration are low.

It is known that ACAT is an enzyme relating to the esterification of cholesterol with higher fatty acids in cells, and plays an important role in the absorption of cholesterol through the small intestine and accumulation of cholesterol ester in the cells. Accordingly, ACAT inhibitors can inhibit the absorption of dietary cholesterol through the intestinal tract, restrain the rise of blood cholesterol level, restrain the accumulation of cholesterol ester in the cells at the atherosclerotic lesion and therefore prevent the progress of atherosclerosis.

The compounds (I) of the present invention are useful as a safe drug for preventing and treating hypercholesterolemia, atherosclerosis and diseases caused thereby (e.g., ischemic cardiac diseases such as myocardial infarction, cerebrovascular disturbances such as cerebral infarction, cerebral apoplexy, etc.) in mammals (e.g., mouse, rat, hamster, rabbit, cat, dog, horse, cattle, sheep, monkey, human, etc.).

Thus, according to one aspect of the invention, it provides an ACAT inhibitory composition comprising a compound (I) or its salt (preferably pharmaceutically acceptable salt) as an active ingredient and a pharmaceutically acceptable carrier, diluent or excipient. Any conventional pharmaceutically acceptable carriers, diluents or excipients can be used. Suitable examples thereof are lactose, starch, water or the like. The ACAT inhibitory compositions may be oral preparations (e.g., powders, granules, tablets or capsules) or parenteral preparations (e.g., injection). These preparations can be easily prepared by utilizing conventional means known in the art. The compound (I) is preferably administered orally when it is used for the purpose of inhibiting the absorption of cholesterol. Dosage of the compound (I) depends on the kind of the compound, administration route, condition and age of the patient, etc. For example, when a compound (I) is administered orally to an adult patient having hypercholesterolemia, a daily dose of about 0.005-50 mg, preferably about 0.05-10 mg, more preferably about 0.2-4 mg of the comopund is administered per 1 kg of weight of the patient, preferably divided into 1-3 times.

The quinoline compounds (II) as the starting materials for the compounds (I) can be prepared by methods known in the art but may be industrially advantageously prepared e.g., by the following method. Compounds as described below may be their salts similar to those of the compounds (I), (II) and (III).

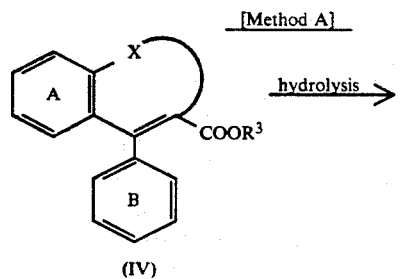

(IV)

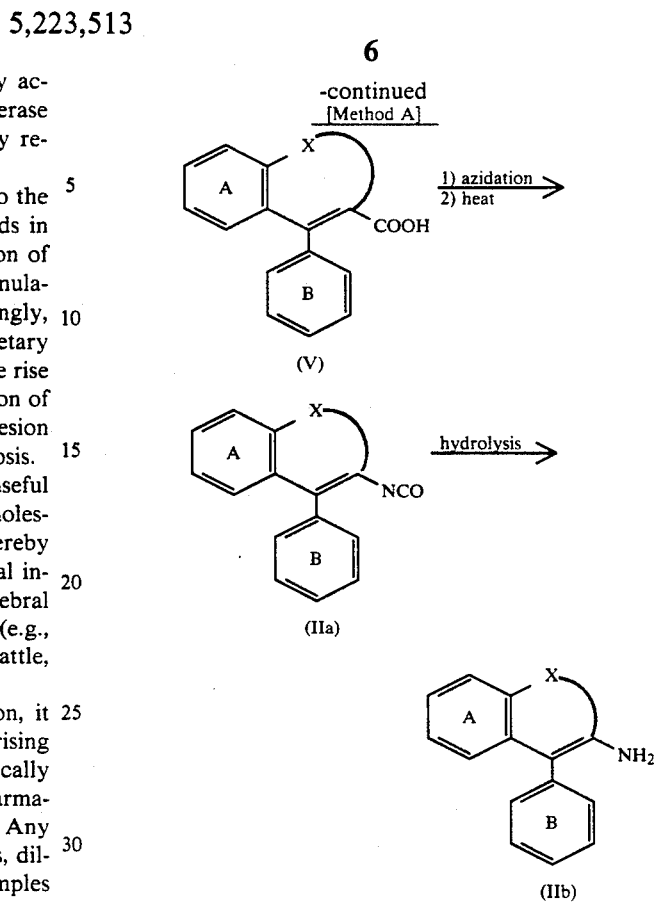

In the formula, $R^3$ is a lower alkyl and the other symbols have the same meanings as defined above.

Examples of the lower alkyl groups for $R^3$ in the compound (IV) are ones having 1-5 carbon atoms, such as methyl, ethyl, propyl, isopropyl, butyl, isobutyl, sec-butyl or tert-butyl.

In the method, the quinoline-3-carboxylic acid ester (IV) is hydrolyzed to give the carboxylic acid (IV), which then is subjected to azidation and heating to convert into the 3-isocyanate derivative (IIa). The hydrolysis of the compound (IV) can be usually conducted by using an alkali metal or alkali earth metal hydroxide (e.g., sodium hydroxide, potassium hydroxide or barium hydroxide) in a solvent (e.g., alcohols such as methanol, ethanol and propanol, or ethers such as dioxane, tetrahydrofuran and dimethoxyethane). The reaction temperature is about 0° C.-100° C., preferably about 20° C.-80° C. The alkali is used in about 1-5 equivalents, to the compound (IV).

Any known methods for converting a carboxylic acid to an acid azide can be applied for the compound (V). For example, the compound (V) can be converted to the corresponding acid azide by using diphenylphosphoryl azide (DPPA) as an azidating agent. This reaction can be usually carried out in an inert solvent (e.g., ethers such as ethyl ether, isopropyl ether, dimethoxyethane, tetrahydrofuran and dioxane; aromatic hydrocarbons such as benzene, toluene and xylene; esters such as methyl acetate and ethyl acetate, ketones such as acetone and methyl ethyl ketone; or pyridine or N,N-dimethylformamide). The reaction may be conducted in the presence of a base (e.g., triethylamine, tributylamine or N-methylmorpholine). The reaction is usually carried out at about 0° C.-200° C., preferably at about 10° C.-100° C. The amount of DPPA to be used is usually about 1-2 equivalents, preferably about 1-1.5 equivalents, to the compound (V). Thus produced acid azide is usually converted to the isocyanatoquinoline (IIa) without isolation by heating, although the acid azide can be isolated and purified by a conventional method. This conversion reaction is preferably carried out in a solvent used for the azidation. The conversion reaction is carried out under heating usually at about 60° C.-200° C., preferably at about 60° C.-150° C. The thus produced compound (IIa) can be isolated by a known method or used as the starting material for preparing the compound (I) or used to prepare another starting material, amino compound (IIb).

That is, the compound (IIa) can be converted into the compound (IIb) upon hydrolysis. The hydrolysis can be usually conducted by using an alkali (e.g., sodium hydroxide, potassium hydroxide or barium hydroxide) in a solvent (e.g., alcohols such as methanol, ethanol and propanol; ethers such as dioxane, tetrahydrofuran and dimethoxyethane; and other solvents mentioned in the azidation). The reaction temperature is about 0° C.-150° C., preferably about 10° C.-100° C., and the amount of the alkali to be used is about 1-5 equivalents to the compound (IIa).

In addition, the compound (IIb) can also be prepared by the method disclosed in U.S. Pat. No. 3,202,661.

The compound (IV) can be prepared e.g., by the following methods.

[Method B]

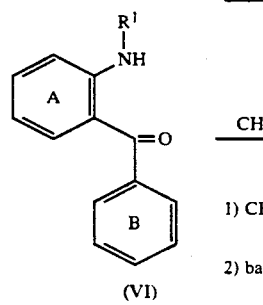

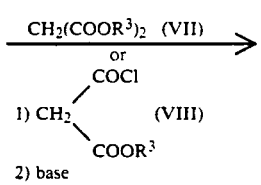

(VI)

[Method B]
-continued

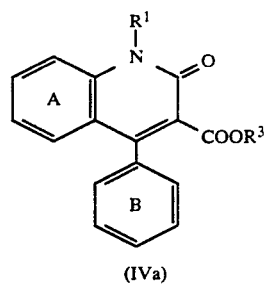

(IVa)

(the symbols have the same meanings as defined above)

[Method C]

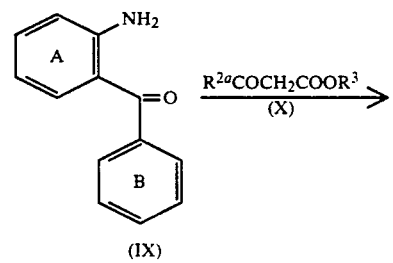

(IX)

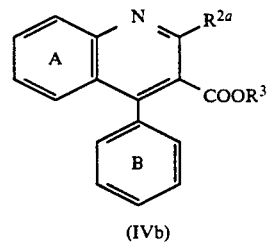

(IVb)

($R^{2a}$ is a lower alkyl groups and the other symbols have the same meanings as defined above)

[Method D]

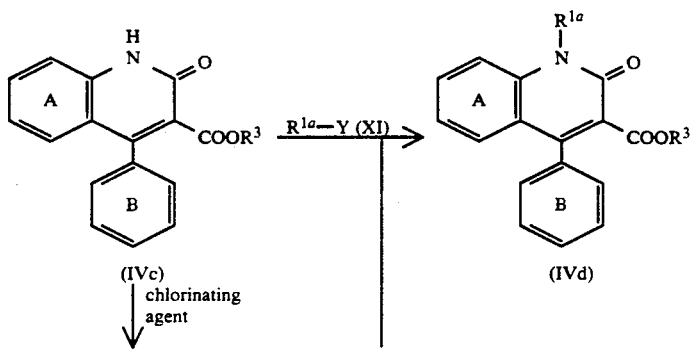

(IVc)  ↓ chlorinating agent (IVd)

-continued

[Method D]

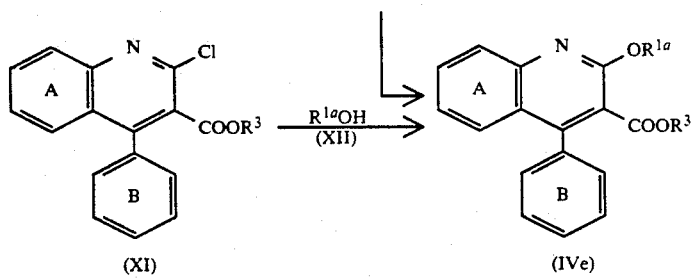

($R^{1a}$ is a lower alkyl group, Y is a leaving group and the other symbols have the same meanings as defined above.)

[Method E]

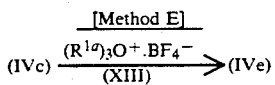

($R^{1a}$ is as defined above.)

The lower alkyl groups mentioned in $R^1$ and $R^2$ are applicable to the lower alkyl groups for $R^{1a}$ and $R^{2a}$ of the above formulae. Examples of the leaving groups are a halogen (e.g., chlorine, bromine or iodine), a $C_{1-4}$ alkylsulfonyloxy group (e.g., methanesulfonyloxy or ethanesulfonyloxy), a $C_{1-10}$ arylsulfonyloxy (e.g., benzenesulfonyloxy or p-toluenesulfonyloxy) or a $C_{1-4}$ alkoxysulfonyloxy group (e.g., methoxysulfonyloxy or ethoxysulfonyloxy).

METHOD B

The 2-aminobenzophenone derivative (VI) is firstly reacted with the malonic acid diester (VII), or with the compound (VIII) followed by the reaction with a base, thereby affording the ring-closed product (IVa).

The reaction of the compound (VI) with the compound (VII) to give the compound (IVa) is usually conducted under heating without any solvent, preferably in the presence of a base such as piperidine, pyrrolidine or triethylamine. The reaction temperature is usually about 100° C.-200° C., preferably about 130° C.-170° C. The amount of the compound (VII) to be used is about 1-5 equivalents, preferably about 1-3 equivalents to the compound (VI). The base is used in about 0.1-1 equivalent to the compound (VI).

The reaction of the compound (VI) with the compound (VIII) is usually conducted in a solvent (e.g., ethers such as ethyl ether dioxane, tetrahydrofuran and dimethoxyethane; esters such as methyl acetate and ethyl acetate; halogenated hydrocarbons such as dichloro- methane and chloroform; aromatic hydrocarbons such as benzene and toluene; pyridine or dimethylformamide), optionally in the presence of a base (e.g., triethylamine, pyridine, potassium carbonate, sodium carbonate, potassium hydrogen carbonate or sodium hydrogen carbonate) and water. The amount of the compound (VIII) to be used is about 1-5 equivalents, preferably 1-2 equivalents, to the compound (VI), and the amount of the base is about 1-5 equivalents, preferably about 1-2 equivalents, to the compound (VI). The reaction temperature is usually about 0° C.-100° C., preferably about 0° C.-60° C. The reaction gives the compound (XIV).

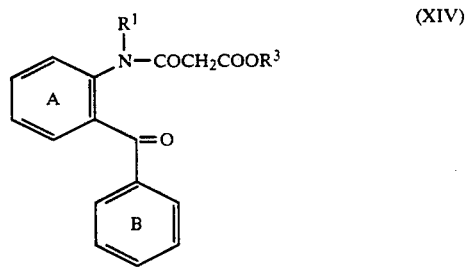

wherein the symbols have the same meanings as defined above. The compound (XIV) with or without isolation is reacted with a base to give the ring-closed product (IVa). The ring-closure reaction is usually conducted in a solvent (e.g., benzene, toluene, xylene, tetrahydrofuran, dioxane or dimethoxyethane). Examples of the bases are potassium t-butoxide, sodium methoxide, sodium ethoxide, piperidine, pyrrolidine, triethylamine, 1,5-diazabicyclo[4.3.0]non-5-en (DBN), 1,8-diazabicyclo[5.4.0]-7-undecene (DBU) and 1,4- diazabicyclo[2.2.2]octane (DABCO). The reaction temperature is usually about 0° C.-200° C., preferably about 20° C.-150° C., although it varies depending upon the kind of the base. The base is used in about 0.1-2 equivalents, preferably about 0.1-1.5 equivalents, to the compound (XIV). The reaction is also conducted by removing the resulting water by use of Dean-Stark's apparatus, for acceleration purposes.

METHOD C

The method comprises reacting the compound (IX) with the acylacetic acid ester (X) to give the compound (IVb). The reaction is usually conducted in a solvent (e.g., alcohols such as methanol, ethanol and propanol; ethers such as tetrahydrofuran, dioxane and dimethoxyethane; organic acids such as formic acid, acetic acid and propionic acid; dimethylformamide or dimethyl sulfoxide) in the presence of an acid catalyst (e.g., mineral acids such as hydrochloric acid, sulfuric acid and phosphoric acid; and sulfonic acids such as methanesulfonic acid, ethansulfonic acid, camphorsulfonic acid, benzenesulfonic acid and toluenesulfonic acid). The reaction temperature is usually about 10° C.-200° C., preferably about 20° C.-150° C. The amount of the compound (X) to be used is about 1-10 equivalents, preferably about 1-3 equivalents, to the compound (IX). The acid catalyst is usually used in about 0.001-2 equivalents, preferably about 0.01-1 equivalents, to the compound (IX).

METHOD D

The method involves the alkylation of the compound (IVc) with the compound (XI) to give the N-alkyl compound (IVd) and/or O-alkyl compound (IVe). The reaction is usually conducted in a solvent (e.g., alcohols such as methanol and ethanol; ethers such as tetrahydrofuran, dioxane and dimethoxyethane; dimethylformamide or dimethyl sulfoxide) in the presence of a base (e.g., sodium hydroxide, potassium hydroxide, sodium methoxide, sodium ethoxide, potassium t-butoxide, sodium amide, potassium carbonate or sodium carbonate). As the procedure for this reaction, the base is added to a solution of the compound (IVc) to give the corresponding salt, which is then reacted with the compound (XI). Alternatively, the reaction can be conducted in such a way that the base and the compound (XI) are added simultaneously to the compound (IVc). Usually, the reaction product is a mixture of the compounds (IVd) and (IVe), which can be separated by recrystallization or chromatography. Also, either one of the compounds (IVd) and (IVe) may predominantly be produced, depending upon the kind of the compound (IVc) and reaction condition. The reaction temperature is usually about 0° C.-150° C., preferably about 10° C.-60° C. Each amount of the base and the compound (XI) to be used is usually about 1-3 equivalents, preferably 1-1.5 equivalents, to the compound (IVc).

Also, the compound (IVe) can be prepared by chlorinating the compound (IVc) with a chlorinating agent and reacting the resultant with the alcohol (XII). Examples of the chlorinating agents for (IVc) are thionyl chloride, phosphorus oxychloride, phosphorus trichloride and phosphorus pentachloride, among which phosphorus oxychloride is preferable. The chlorination is usually conducted under heating to about 50° C.-150° C., preferably about 70° C.-120° C. without any solvent. However, it can be conducted in an inert solvent (e.g., chloroform, benzene, toluene and xylene) and in the presence of pyridine, N,N-dimethylformamide or the like which can accelerate the reaction, if required. The amount of the chlorinating agent to be used is usually about 1-50 equivalents, preferably 1-20 equivalents to the compound (IVc). The resulting product (XI) can be isolated and purified but can be directly used to react with the compound (XII) to afford the compound (IVe). The reaction of the compound (XI) with the compound (XII) is preferably conducted in the presence of a base (e.g., an alkoxide of RlaOH with a metal). Examples of the metals to form such alkoxide are sodium or potassium. The amount of the metal alkoxide to be used is usually about 1-5 equivalents, preferably about 1-3 equivalents to the compound (XI). The reaction temperature is usually about 20° C.-120° C., preferably about 50° C.-100° C. Also, the compound (XII) itself can be preferably used as the solvent.

METHOD E

In this method, the compound (IVe) can be prepared by reacting the compound (IVc) with the trialkyloxonium fluoroborate (XIII). The reaction is usually conducted in a solvent (e.g., dichloromethane or chloroform) about 0° C.-60° C., preferably about 15° C.-40° C. The compound (XIII) is usually used in about 1-10 moles, preferably about 1-3 moles to the compound (IVc).

Activity

Pharmacological test results on the compounds (I) and their salts of the present invention are shown in the following.

1. Acyl-CoA : Cholesterol Acyltransferase (ACAT) inhibitory activity

Methods

The enzyme ACAT was prepared by the method of Heider et al. described in Journal of Lipid Research, Vol. 24, page 1127 (1982), from the mucosal microsome fraction of the small intestine of male, 6-week old Sprague-Dawley rats which had been fasted for 20 hours.

ACAT activity was calculated by the method of Helgerud et al. described in Journal of Lipid Research, Vol. 22, page 271 (1981), namely, by measuring the amount of the labeled cholesterol ester produced from [1-$^{14}$C] oleoyl-CoA and endogenous cholesterol.

Results

Inhibition rates (%) of the production of the labeled cholesterol ester wherein $10^{-6}$M of test compounds were added are shown as an index of ACAT inhibitory activity in Table 1. Also, Table 1 shows 50% inhibitory concentration (IC$_{50}$) which was calculated by plotting inhibition rates obtained at plural concentrations.

TABLE 1

| Test Compound (Example No.) | ACAT Inhibition Rate (%) | IC$_{50}$(M) |
|---|---|---|
| 1 | 96.8 | |
| 2 | 99.2 | $1.6 \times 10^{-8}$ |
| 3 | 98.7 | $6.4 \times 10^{-9}$ |
| 4 | 97.1 | |
| 5 | 98.2 | $1.8 \times 10^{-8}$ |
| 6 | 97.9 | |
| 7 | 77.9 | |
| 9 | 89.6 | |
| 10 | 97.6 | $7.8 \times 10^{-8}$ |
| 11 | 96.6 | |
| 12 | 95.9 | |
| 13 | 85.4 | |
| 15 | 90.1 | |
| 17 | 96.5 | $2.5 \times 10^{-8}$ |
| 18 | 99.2 | $1.2 \times 10^{-8}$ |
| 19 | 97.8 | $3.7 \times 10^{-8}$ |
| 20 | 96.1 | $3.5 \times 10^{-8}$ |
| 21 | 99.4 | $1.7 \times 10^{-8}$ |
| 22 | 99.0 | $3.7 \times 10^{-8}$ |
| 23 | 99.0 | $4.1 \times 10^{-8}$ |
| 24 | 99.2 | $9.3 \times 10^{-9}$ |

It is clearly proved through the above Table 1 that the quinoline derivatives (I) and their salts possess excellent ACAT inhibitory activities.

2. Plasma Cholesterol Lowering Activity in Cholesterol Fed Rat

Method

To 7-week old, male Sarague-Dawely rats which were grouped according to body weight was fed 1% cholesterol diet containing 0.5% of cholic acid, 5% of olive oil and 0.0003% of a test compound for 7 days. Blood was collected from the rats during 8:30-10:00 am at the fed state, and the plasma cholesterol level was measured enzymatically. The amount of test compound consumed by rats was calculated on the basis of the amount of the diet consumed by the rats.

Results

Plasma cholesterol level in cholesterol fed rats were significantly lowered by the test compounds as shown in Table 2.

TABLE 2

| Test Compound (Example No.) | Dose (mg/kg/day) | Cholesterol in Serum (mg/dl) |
| --- | --- | --- |
| Control | 0 | 195 ± 32 |
| 3 | 0.27 ± 0.02 | 129 ± 19* |
| 24 | 0.24 ± 0.03 | 113 ± 41* |

The values are mean values ± standard deviations.
*p < 0.05 (t - test vs control group)

It is proved by the above Table 2 that the quinoline derivatives (I) and their salts possess excellent activity for lowering plasma cholesterol.

EXAMPLES

This invention is explained in more detail by the following Reference Examples and Examples. But, it should be noted that this invention is not restricted by these Examples.

In the Reference Examples and Examples, elution of a column chromatography was conducted by observing thin layer chromatography (TLC). The observation of TLC was carried out by using silica gel $60F_{254}$ manufactured by Merck Co., Inc. as a TLC plate and the same solvent as the one used for an eluting solvent in the column chromatography as a developing solvent, and with an UV detector as a detecting means. Silica gel 60 (70-230 mesh) manufactured by Merck Co., Inc. was used as silica gel for the column chromatography.

Abbreviations used in the Examples and Reference Examples have the following meanings.

| | |
| --- | --- |
| mg: milligram, | g: gram, |
| ml: milliliter, | m.p.: melting point |
| Further, room temperature means 15-20° C. | |

EXAMPLE 1

To a solution of 6-chloro-4-(2-chlorophenyl)-1,2-dihydro -1-methyl-2-oxoquinoline-3-carboxylic acid (348 mg) and iphenylphosphoryl azide (330 mg) in benzene (4 ml) was dropwise added triethylamine (0.14 ml) under stirring. The mixture was stirred at room temperature for 20 minutes and under refluxing for 30 minutes to yield a solution of 6-chloro-4-(2-chlorophenyl)-1,2-dihydro-3-isocyanato-1-methyl-2-oxoquinoline. 2,4-Difluoroaniline (0.12 ml) was added to the solution after cooling and stirred at room temperature for 30 minutes and under refluxing for 2 hours. The reaction solution was washed, dried ($MgSO_4$) and concentrated. The residue was crystallized to obtain N-[6-chloro-4-(2-chlorophenyl)-1,2-dihydro-1-methyl-2-oxo-8-quinolyl]-N,-(2,4-difluorophenyl)urea (367 mg, 77.4%). Recrystallization from ethanol gave colorless prisms of mp 204°-206° C.

Elemental analysis for $C_{23}H_{25}Cl_2F_2N_3O_2$:
Calculated : C 58.25; H 3.19; N 8.86;
Found : C 58.54; H 3.06; N 8.90.

By the same method as in Example 1, the compounds of Examples 2-13 were obtained.

EXAMPLE 2

N-[6-chloro-4-(2-chlorophenyl)-1,2-dihydro-1-methyl]-2-oxo-3-quinolyl]-N'-(2-isopropyl-6-methylphenyl)urea : Yield 96.5%. mp 148°-150° C. (recrystallized from ethyl ether)

Elemental analysis for $C_{27}H_{25}Cl_2N_3O_2$: Calculated : C 65.59; H 5.10; N 8.50 ; Found : C 65:58; H5.11; N 8.49.

EXAMPLE 3

N-[4-(2-chlorophenyl)-1,6,7-trimethyl-1,2-dihydro-2-oxo-3-quinolyl]-N'-(2,4-difluorophenyl)urea: Yield 50.3%. mp 242°-244° C. (from ethanol-chloroform)

Elemental analysis for $C_{25}C_{20}ClF_2N_3O_2$ : Calculated : C 64.17; H 4.31; N 8.98 ;Found : C 64.14; H 4.26; N 8.85.

EXAMPLE 4

N-[4-(2-chlorophenyl)-1,2-dihydro-1,6,8-trimethyl-2-oxo-3-quinolyl]-N'-(2,4-difluorophenyl)urea: Yield 66.4%. mp 225°-227° C. (from acetone)

Elemental analysis for $C_{25}C_{20}ClF_2N_3O_2$ : Calculated : C 64.17; H 4.31; N 8.98 ; Found : C 64.22; H 4.32; N 8.99.

EXAMPLE 5

N-[4-(2-chlorophenyl)-1,2-dihydro-1,6,8-trimethyl-2-oxo-3-quinolyl]-N'-(2-isopropyl-6-methylphenyl)urea: Yield 63.9% mp 203°-204° C. (from ethyl acetate - hexane)

Elemental analysis for $C_{29}H_{30}ClN_3O_2$: Calculated : C 71.37; H 6.20; N 8.61 ; Found : C 71.66; H 6.46; N 8.49.

EXAMPLE 6

N-[4-(2-chlorophenyl)-1-ethyl-1,2-dihydro-6,8-dimethyl-2-oxo-3-quinolyl]-N'-(2,4-difluorophenyl)urea: Yield 65.4%. mp 186°-188° C. (from ethanol)

Elemental analysis for $C_{26}H_{22}ClF_2N_3O_2$ : Calculated : C 64.80; H 4.60; N 8.72 ; Found : C 65.09; H 4.58; N 8.44.

EXAMPLE 7

N-(6-chloro-1,2-dihydro-1-methyl-2-oxo-4-phenyl-3-quinolyl)-N'-(2,4-difluorophenyl)urea: Yield 66.2% mp 204°-206° C. (from ethanol)

Elemental analysis for $C_{23}H_{16}ClF_2N_3O_2$ : Calculated : C 62.81; H 3.67; N 9.55 ; Found : C 62.67; H 3.63; N 9.66.

EXAMPLE 8

N-(6-chloro-2-ethoxy-4-phenyl-3-quinolyl)-N'-(2,4difluorophenyl)urea: Yield 61.0% mp 238°-239° C. (from acetone)

Elemental analysis for $C_{24}H_{18}ClF_2N_3O_2$ : Calculated : C 63.51; H 4.00; N 9.26 ; Found : C 63.59; H 3.89; N 9.17.

EXAMPLE 9

N-[6-chloro-4-(2-chlorophenyl)-2-methoxy-3-quinolyl]-N'-2,4-difluorophenyl)urea (1/2 ethanol solvate): Yield 80.1%. mp 217°-218° C. (from ethanol)

Elemental analysis for $C_{23}H_{15}ClF_2C_2)_2 \cdot \frac{1}{2} C_2H_6O$: Calculated : C 57.96; H 3.65; N 8.45; Found : C 57.72; H 3.85; N 8.21.

EXAMPLE 10

N-(2,4-difluorophenyl)-N'-(1,2-dihydro-1,6,7-trimethyl-4-(2-methylphenyl)-2-oxo-3-quinolyl]urea: Yield 79.4%. mp 225°-226° C. (from acetone).

Elemental analysis for $C_{26}H_{23}F_2N_3O_2$ : Calculated : C 69.79; H 5.18; N 9.39 ; Found : C 69.74; H 5.10; N 9.36.

EXAMPLE 11

N-(2,4-difluorophenyl)-N'-[1,2-dihydro-4-(3,4-dimethoxyphenyl) -1,6-dimethyl-2-oxo-3-quinolyl]urea: Yield 83.3%. mp 231°–233° C. (from acetone)

Elemental analysis for $C_{26}H_{23}F_2N_3O_4$: Calculated : C 65.13; H 4.83; N 8.76 ; Found : C 65.22; H 4.80; N 8.77.

EXAMPLE 12

N-[4-(2-chlorophenyl)-2-methoxy-6,8-dimethyl-3-quinolyl]-N -(2,4-difluorophenyl)urea: Yield 89.5% mp 231–232° C. (from acetone)

Elemental analysis for $C_{25}C_{20}ClF_2N_3O_2$ : Calculated : C 64.17; H 4.31; N 8.98 ; Found : C 63.98; H 4.31; N 8.88.

EXAMPLE 13

N-[4-(2-chlorophenyl)-2,6,8-trimethyl-3-quinolyl]-N'-(2,4-difluorophenyl)urea: Yield 86.9%. mp 234°–235° C. (from acetone)

Elemental analysis for $C_{25}C_{20}ClF_2N_3O$: Calculated : C 66.45; H 4.46; N 9.30 ; Found : C 66.43; H 4.50; N 9.23.

EXAMPLE 14

A mixture of 3-amino-6-chloro-4-phenyl-2(1H)-quinolone (160 mg), 2,4-difluorophenylisocyanate (0.09 ml) and anhydrous tetrahydrofuran (2 ml) was allowed to stand overnight at room temperature. The precipitated crystals were collected and recrystallized from dimethylformamide containing water to give colorless needles of N-(6-chloro-1,2-dihydro-2-oxo-4-phenyl-3-quinolyl)-N'-(2,4-difluorophenyl)urea (185 mg, 73.4%). mp 222°–224° C.

Elemental analysis for $C_{22}H_{14}ClF_2N_3O_2$ : Calculated : C 62.05; H 3.31; N 9.87 ; Found : C 62.02; H 3.26; N 9.78.

EXAMPLE 15

To a mixture of 4-acetoxy-3,5-dimethoxybenzoic acid (672 mg), diphenylphosphoryl azide (990 mg) and benzene (15 ml) was dropwise added triethylamine (0.42 ml), while stirring. The mixture was stirred for 20 minutes at room temperature and further for 30 minutes under refluxing to obtain a solution of 4-acetoxy-3,5-dimethoxyphenyl isocyanate in benzene. 3-Amino-4-(2-chlorophenyl)-1,6,7-trimethyl-2(1H)-quinolone (624 mg) was added to the above solution and the mixture was refluxed for 2.5 hours. The mixture was washed with water, aqueous sodium hydrogen carbonate solution, water, diluted hydrochloric acid and then water in this order, dried (MgSO$_4$) and concentrated.

The residue was recrystallized from ethanol isopropyl ether to give crystals of N-(4-acetoxy-3,5-dimethoxyphenyl) -N'-[4-(2-chlorophenyl)-1,2-dihydro-1,6,7-trimethyl-2-oxo-3-quinolyl]urea (840 mg, 76.4%). Further recrystallization from acetone - isopropyl ether gave colorless needles. mp 233°–234° C.

Elemental analysis for $C_{29}H_{28}ClN_3O_6$: Calculated : C 63.33; H 5.13; N 7.64 ; Found : C 63.43; H 5.19; N 7.56.

EXAMPLE 16

To a solution of N-(2,4-difluorophenyl)-N'-[1,2-dihydro -4-(3,4-dimethoxyphenyl)-1,6-dimethyl-2-oxo-3-quinolyl]urea (0.35 g) in dichloromethane (10 ml) was dropwise added a solution of boron tribromide - dichloromethane (1:2, 1.0 ml) under ice-cooling and stirring.

The mixture was continued to stirred for an hour under ice-cooling and then poured to ice-water. The mixture was extracted with ethyl acetate. The extract was washed with water, dried (MgSO$_4$) and concentrated to obtain crystals of N-(2,4-difluorophenyl)-N'-[1,2-dihydro-4-(3,4-dihydroxyphenyl) -1,6-dimethyl-2-oxo-3-quinolyl]urea. Recrystallization from ethanol gave colorless needles (0.25 g, 75.8%). mp 204°–205° C.

Elemental analysis for $C_{24}H_{19}F_3N_3O_4$: Calculated : C 63.86; H 4.24; N 9.31 ; Found : C 63.59; H 4 19; N 9.24.

By the same method as in Example 1, the compounds of Examples 17–24 were obtained.

EXAMPLE 17

N-[4-(2-chlorophenyl)-1,2-dihydro-6-ethyl-1-methyl-2-oxo-3-quinolyl]-N'-(2,4-difluorophenyl)urea: Yield 84.6% mp 192°–195° C. (from ethanol - hexane)

Elemental analysis for $C_{25}C_{20}ClF_2N_3O_3$ : Calculated : C 64.17; H 4.31; N 8.98 ; Found : C 64.40; H 4.29; N 8.70.

EXAMPLE 18

N-[4-(2-chlorophenyl)-1,2-dihydro-6-ethyl-1-methyl-2-oxo -3-quinolyl]-N'-(2-isopropyl-6-methylphenyl)urea: Yield 88.7%. mp 198°–199° C. (from ethanol)

Elemental analysis for $C_{29}H_{30}ClN_3O_2$: Calculated : C 71.37; H 6.20; N 8.61 ; Found : C 71.57; H 6.30; N 8.57.

EXAMPLE 19

N-[4-(2-chlorophenyl)-1,2-dihydro-6-isopropyl-1-methyl -2-oxo-3-quinolyl]-N'-(2,4-difluorophenyl)urea (⅓ hexane solvate): Yield 70.6%. mp 152°–156° C. (from ethanol - hexane)

Elemental analysis for $C_{25}C_{20}ClF_2N_3O_2 \cdot \tfrac{1}{3}C_6H_{14}$ : Calculated : C 65.91; H 5.19; N 8.23; Found : C 66.09; H 5.26; N 8.27.

EXAMPLE 20

N-[6-chloro-1,2-dihydro-1-methyl-4-(2-methylphenyl)-2-oxo-3-quinolyl]-N'-(2,4-difluorophenyl)urea: Yield 85.0%. mp 163°–165° C. (from ethanol - hexane)

Elemental analysis for $C_{24}H_{18}ClF_2N_3O_2$ : Calculated : C 63.51; H 4.00; N 9.26 ; Found : C 63.73; H 4.23; N 8.94.

EXAMPLE 21

N-[6-chloro-1,2-dihydro-1-methyl-4-(2-methylphenyl)-2-oxo-3-quinolyl]-N'-(2-isopropyl-6-methylphenyl)urea: Yield 83.5%. mp 195°–196° C. (from ethanol - hexane)

Elemental analysis for $C_{28}H_{28}ClN_3O_2$: Calculated : C 70.95; H 5.95; N 8.86 ; Found : C 70.95; H 6.14; N 8.67.

EXAMPLE 22

N-[1,2-dihydro-4-(3,4-dimethoxyphenyl)-1,6-dimethyl-3-quinolyn]-N'-(2-isopropyl-6-methylphenyl)urea: Yield 90.6%. mp 190°–193° C. (from ethanol - isopropyl ether)

Elemental analysis for $C_{30}H_{33}N_3O_4$: Calculated : C 72.12; H 6.66; N 8.41 ; Found : C 72.17; H 7.00; N 8.07.

EXAMPLE 23

N-[6-chloro-1,2-dihydro-4-(3,4-dimethoxyphenyl)-1-methyl-3-quinolyl]-N'-(2-isopropyl-6-methylphenyl)urea (½hydrate): Yield 77.5%. mp 200°–201° C. (from ethanol)

Elemental analysis for $C_{29}H_{30}ClN_3O_4 \cdot \frac{1}{2}H_2O$: Calculated : C 65.84; H 5.91; N 7.94 ; Found : C 65.99; H 5.86; N 7.91.

EXAMPLE 24

N-[7-chloro-1,2-dihydro-4-(2-methylphenyl)-1,6-dimethyl -2-oxo-3-quinolyl]-N'-(2,4-difluorophenyl-)urea: Yield 93.1%. mp 227°–229° C. (from ethanol - chloroform)

Elemental analysis for $C_{25}H_{20}ClF_2H_3O_2$: Calculated : C 64.17; H 4.31; N 8.98; Found : C 63.91; H 4.54; N 9.16.

EXAMPLE 25

A mixture of 3-amino-4-(2-chlorophenyl)-1,6,7-trimethyl-2(1H)-quinolone (156 mg), 4-chlorophenyl isocyanate (115 mg) and benzene (4 ml) was refluxed for 1.5 hours and then distilled to remove the solvent. The remaining crystals as collected by filtration were washed with isopropyl ether to obtain N-(4-chlorophenyl)-N'-[4-(2-chlorophenyl) -1,2-dihydro-1,6,7-trimethyl-2-oxo-3-quinolyl]urea (188 mg, 80.7%). Recrystallization from acetone - hexane gave colorless needles. mp 207°–209° C.

Elemental analysis for $C_{25}H_{21}Cl_2H_3O_2$: Calculated : C 64.39; H 4.54; N 9.01; Found : C 64.11; H 4.54; N 8.86.

By the same method as in Example 25, the compounds of Examples 26–29 were obtained.

EXAMPLE 26

N-[4-(2-chlorophenyl)-1,2-dihydro-1,6,7-trimethyl-2-oxo-3-quinolyl]-N'-(3-trifluoromethylphenyl)urea: Yield 88.8%. mp 175°–176° C. (from ethanol)

Elemental analysis for $C_{26}H_{21}ClF_3H_3O_2$: Calculated : C 62.47; H 4.23; N 8.41; Found : C 62.36; H 4.28; N 8.37.

EXAMPLE 27

N-[4-(2-chlorophenyl)-1,2-dihydro-1,6,7-trimethyl-2-oxo-3-quinolyl]-N'-phenylurea: Yield 41.4%. mp 218°–219° C. (from acetone)

Elemental analysis for $C_{26}H_{22}ClH_3O_2$: Calculated : C 69.52; H 5.13; N 9.73; Found : C 69.50; H 5.20; N 9.72.

EXAMPLE 28

N-[4-(2-chlorophenyl)-1,2-dihydro-1,6,7-trimethyl-2-oxo-3-quinolyl]-N'-(3-methylphenyl)urea: Yield 73.0%. mp 210°–211° C. (from acetone)

Elemental analysis for $C_{26}H_{24}ClH_3O_2$: Calculated : C 70.03; H 5.42; N 9.42; Found : C 69.86; H 5.67; N 9.35.

EXAMPLE 29

N-[4-(2-chlorophenyl)-1,2-dihydro-1,6,7-trimethyl-2-oxo-3-quinolyl]-N'-(3-nitrophenyl)urea: Yield 73.5% mp 190°–192° C. (from acetone)

Elemental analysis for $C_{25}H_{24}ClN_4O_4$: Calculated : C 62.96; H 4.44; N 11.75; Found : C 62.82; H 4.35; N 11.65.

By the same method as in Example 1, the compounds of Examples 30–33 were obtained.

EXAMPLE 30

N-(3-chlorophenyl)-N'-[4-(2-chlorophenyl)-1,2-dihydro -1,6,7-trimethyl-2-oxo-3-quinolyl]urea ($\frac{1}{2}$ ethanol solvate): Yield 78.7%. mp 208°–210° C. (from ethanol)

Elemental analysis for $C_{25}H_{21}Cl_2N_3O_2 \cdot \frac{1}{2} C_2H_6O$: Calculated : C 63.81; H 4.94 ; N 8.59; Found : C 63.93; H 4.95; N 8.62.

EXAMPLE 31

N-[4-(2-chlorophenyl)-1,2-dihydro-6-isopropyl-1-methyl -2-oxo-3-quinolyl]-N'-(3-trifluoromethylphenyl-)urea: Yield 78.1%. mp 209°–210 ° C. (from acetone - hexane)

Elemental analysis for $C_{27}H_{23}ClF_3H_3O_2$: Calculated : C 63.10; H 4.51; N 8.81; Found : C 63.40; H 4.55; N 8.12.

EXAMPLE 32

N-[4-(2-chlorophenyl)-2,6,8-trimethyl-3-quinolyl]-N'-(3-trifluoromethylphenyl) urea: Yield 87.6%. mp 146°–147° C. (from acetone - hexane)

Elemental analysis for $C_{26}H_{21}ClF_3N_3O$: Calculated : C 64.53; H 4.37; N 8.68; Found : C 64.75; H 4.24; N 8.67.

EXAMPLE 33

N-[4-(2-chlorophenyl)-2-methoxy-6,8-dimethyl-3-quinolyl]-N'-(3-trifluoromethylphenyl)urea: Yield 91.4%. mp 151°–153° C. (from acetone - hexane)

Elemental analysis for $C_{26}H_{21}ClF_3H_3O_2$: Calculated : C 62.47; H 4.23; N 8.41; Found : C 62.64; H 4.64; N 8.10.

REFERENCE EXAMPLE 1

A mixture of 2-amino-5,2,-dichlorobenzophenone (3.99 g), diethyl malonate (3.6 g) and piperidine (0.3 ml) was heated at 170° C. for 15 hours. After cooling, ethanol was added to the reaction mixture to give crystals of ethyl 6-chloro-4-(2-chlorophenyl)-1,2-dihydro-2-oxo-3-quinolinecarboxylate (3.60 g, 66.3%). Recrystallization from ethanol - chloroform gave colorless prisms. mp 223°–224° C.

Elemental analysis for $C_{18}H_{13}Cl_2NO_3$: Calculated : C 59.69; H 3.62; N 3.87; Found : C 59.75; H 3.62; N 3.92.

REFERENCE EXAMPLE 2

To a mixture of ethyl 6-chloro-4-(2-chlorophenyl)-1,2-dihydro-2-oxo-3-quinolinecarboxylate(1.81 g), potassium carbonate powder (0.7 g), and N,N-dimethylformamide (DMF) (20 ml) was dropwise added methyl iodide (0.37 g) under stirring. The mixture was stirred for 2.5 hours, diluted with water and then extracted with ethyl acetate. The extract was washed with water, dried ($MgSO_4$) and distilled to remove the solvent. The residue was crystallized with isopropyl ether to obtain ethyl 6-chloro-4-(2-chlorophenyl)-1,2-dihydro-1-methyl-2-oxo-3-quinolinecarboxylate. Recrystallization from ethanol gave colorless prisms. mp 139°–140° C.

Elemental analysis for $C_{18}H_{15}Cl_2NO_3$: Calculated : C 60.66; H 4.02; N 3.72; Found : C 60.65; H 4.00; N 3.72.

REFERENCE EXAMPLE 3

A mixture of ethyl 6-chloro-4-(2-chlorophenyl)-1,2-dihydro -1-methyl-2-oxoquinoline-3-carboxylate (1.3 g), ethanol (6.0 ml) and potassium hydroxide (0.6 g) was refluxed for 15 minutes. The mixture was diluted with water and acidified by addition of 2N-hydrochloric acid. The precipitated crystals were collected and recrystallized from ethanol to obtain colorless plates of 6-chloro-4-(2-chlorophenyl) -1,2-dihydro-1-methyl-2-oxo-3-quinolinecarboxylic acid (1.20 g, 85.0%). mp 197°–198° C.

Elemental analysis for $C_{17}H_{11}Cl_2NO_3$: Calculated : C 58.64; H 3.18; N 4.02; Found : C 58.66; H 3.10; N 4.02.

REFERENCE EXAMPLE 4

To a mixture of 2-amino-2'-chloro-1,5-dimethylbenzophenone (4.0 g), triethylamine (4.3 ml) and ethyl acetate (80 ml) was dropwise added methyl malonyl chloride (3.77 g) under ice-cooling and stirring. The stirring was continued for an hour under ice-cooling. The reaction mixture was washed with water, dried (MgSO$_4$) and distilled to remove the solvent. The oily residue was dissolved in toluene (60 ml), followed by addition of piperidine (0.4 ml). The solution was heated for an hour with removal of water using Dean-Stark's apparatus. Then, the solution was washed with water, dried (MgSO$_4$) and concentrated to obtain crystals of methyl 4-(2-chlorophenyl)-1,2-dihydro-6,7-dimethyl-2-oxo-3-quinolinecarboxylate (4.40 g, 83.7%). Recrystallization from ethanol - chloroform gave colorless prisms. mp 288°–289° C.

Elemental analysis for C$_{19}$H$_{16}$ClNO$_3$: Calculated : C 66.77; H 4.72; N 4.10; Found : C 66.52; H 4.62; N 4.05.

REFERENCE EXAMPLE 5

Methyl 4-(2-chlorophenyl)-1,2-dihydro-6,7-dimethyl-2-oxo-3-quinolinecarboxylate was methylated in the same way as in Reference Example 2 to obtain methyl 4-(2-chlorophenyl) -1,2-dihydro-1,6,7-trimethyl-2-oxo-3quinolinecarboxylate. Yield 80.3%. mp 202°–203° C. (from ethanol)

Elemental analysis for C20H18ClNO$_3$: Calculated : C 67.51; H 5.10; N 3.94; Found : C 67.65; H 5.08; N 3.85.

REFERENCE EXAMPLE 6

Methyl 4-(2-chlorophenyl)-1,2-dihydro-1,6,7-trimethyl -2-oxo-3-quinolinecarboxylate was hydrolyzed by the same method as in Reference Example 3 to obtain 4-(2-chloro-phenyl) -1,2-dihydro-1,6,7-trimethyl-2-oxo-3-quinolinecarboxylic acid. Yield 93.8%. mp 251°–252° C. (from chloroform - ethanol)

Elemental analysis for C$_{19}$H$_{16}$ClNO$_3$: Calculated : C 66.77; H 4.72; N 4.10; Found : C 67.00; H 4.68; N 4.10.

REFERENCE EXAMPLE 7

To a mixture of 2'-chloro-3,5-dimethyl-2-methylaminobenzophenone (5.0 g), triethylamine (7.8 ml) and ethyl acetate (100 ml) was dropwise added methyl malonyl chloride (6.7 g) under ice-cooling and stirring, followed by stirring for 1.5 hours.

The mixture was washed with water, dried (MgSO$_4$) and distilled to remove the solvent. The oily residue was dissolved in tetrahydrofuran (50 ml), to which potassium t-butoxide (2.3 g) was added in small portions under ice-cooling and stirring. The mixture was stirred for 30 minutes under ice-cooling. 2N-Hydrochloric acid (10 ml) was added, and the mixture was diluted with water and extracted with ethyl acetate. The extract was washed with water, dried (MgSO$_4$) and purified by chromatography on silica gel (100 g) using benzene - acetone (4:1, v/v), to obtain methyl 4-(2-chlorophenyl)-1,2-dihydro -1,6,8-trimethyl-2-oxo-3-quinolinecarboxylate (3.85 g, 59.2%). Recrystallization from ethanol gave colorless prisms. mp 128°–129° C.

Elemental analysis for C$_{20}$H$_{18}$ClNO$_3$: Calculated : C 67.51; H 5.10; N 3.94; Found : C 67.37; H 5.07; N 3.92.

REFERENCE EXAMPLE 8

By the same method as in Reference Example 3, methyl 4-(2-chlorophenyl)-1,2-dihydro-1,6,8-trimethyl-2-oxo-3-quinolinecarboxylate was hydrolyzed to obtain 4-(2-chlorophenyl) -1,2-dihydro-1,6,8-trimethyl-2-oxo-3-quinolinecarboxylic acid. Yield 76.5%. mp 162°–163° C. (from ethanol)

Elemental analysis for C$_{19}$H$_{16}$ClNO$_3$: Calculated : C 66.77; H 4.72; N 4.10; Found : C 66.72; H 4.71; N 4.11.

REFERENCE EXAMPLE 9

To a solution of methyl 4-(2-chlorophenyl)-1,2-dihydro -6,7-dimethyl-2-oxoquinoline-3-carboxylate in DMF (20 ml) was added portionwise 60% sodium hydride in oil (0.21 g), and the mixture was stirred at room temperature for 20 minutes. Ethyl iodide (0.48 ml) was dropwise added to the mixture. The resulting mixture was diluted with water and extracted with ethyl acetate. The extract was washed with water dried (MgSO$_4$) and distilled to remove the solvent. The oily residue was purified by chromatography on silica gel (40 g) using benzene - acetone (4:1, v/v) to obtain methyl 4-(2-chlorophenyl-1-ethyl-1,2-dihydro -6,7-dimethyl-2-oxo-3-quinolinecarboxylate as crystals. Recrystallization from ethanol gave colorless prisms. mp 172°–173° C.

Elemental analysis for C$_{21}$H$_{20}$ClNO$_3$: Calculated : C 68.20; H 5.45; N 3.79; Found : C 68.28; H 5.51; N 3.72.

REFERENCE EXAMPLE 10

By the same method as in Reference Example 3, methyl 4-(2-chlorophenyl)-1-ethyl-1,2-dihydro-6,7-dimethyl-2-oxo -3-quinolinecarboxylate was hydrolyzed to obtain 4-(2-chlorophenyl) -1-ethyl-1,2-dihydro-6,7-dimethyl-2-oxo-3-quinolinecarboxylic acid. Yield 92.5%. mp 168°–170° C. (from chloroform - ethanol)

Elemental analysis for C$_{20}$H$_{18}$ClNO$_3$: Calculated : C 67.51; H 5.10; N 3.94; Found : C 67.48; H 5.09; N 3.97.

REFERENCE EXAMPLE 11

A mixture of 2-amino-5-chlorobenzophenone (6.93 g), diethyl malonate (7.2 g) and piperidine (0.3 ml) was heated at 170° C. for 4 hours. After cooling, isopropyl ether was added to the mixture to obtain crystals of ethyl 6-chloro-1,2-dihydro-2-oxo-4-phenyl-3-quinolinecarboxylate (7.77 g, 79.3%). The crystals was recrystallized from ethanol to give pale-yellowish needles. mp 223°–224° C.

Elemental analysis for C$_{18}$H14ClNO$_3$: Calculated : C 65.96; H 4.31; N 4.27; Found : C 66.01; H 4.31; N 4.40.

REFERENCE EXAMPLE 12

To a mixture of ethyl 6-chloro-1,2-dihydro-2-oxo-4-phenyl-3-quinolinecarboxylate (2.62 g) and DMF (24 ml) was added portionwise 60% sodium hydride in oil (0.35 g), followed by stirring for 30 minutes at room temperature. The mixture was ice-cooled, to which methyl iodide (0.6 g) was dropwise added under stirring. The mixture was stirred for 3 hours at room temperature, diluted with and extracted with ethyl acetate. The extract was washed with water, dried (MgSO$_4$) and concentrated to remove the solvent. The residue was crystallized from isopropyl ether to give crystals of ethyl 6-chloro-1,2-dihydro -1-methyl-2-oxo-4-phenyl-3-quinolinecarboxylate (2.35 g, 92.7%). Recrystallization from ethanol gave colorless needles. mp 124°–125° C.

Elemental analysis for C$_{19}$H$_{16}$ClNO$_3$: Calculated : C 66.77; H 4.72; N 4.10; Found : C 66.72; H 4.72; N 3.97.

REFERENCE EXAMPLE 13

A mixture of 5-chloro-2-methylaminobenzophenone (1.23 g), diethyl malonate (1.6 g) and piperidine (0.1 ml)

was heated for 3 hours at 170°-180° C. After cooling, the mixture was treated with isopropyl ether to give crystals, which were recrystallized from ethanol to afford ethyl 6-chloro-1,2-dihydro-1-methyl-2-oxo-4-phenyl-3-quinolinecarboxylate (1.25 g, 73.1%). mp 124°-125° C. The product was identical with the compound obtained in Reference Example 12.

REFERENCE EXAMPLE 14

By the same method as in Reference Example 3, ethyl 6-chloro-1,2-dihydro-1-methyl-2-oxo-4-phenyl-3-quinolinecarboxylate was hydrolyzed to obtain 6-chloro-1,2-dihydro-1-methyl -2-oxo-4-phenyl-3-quinolinecarboxylic acid. Yield 96.7%. mp 242°-243° C.

Elemental analysis for $C_{17}H_{12}ClNO_3$: Calculated : C 65.08; H 3.86; N 4.46; Found : C 64.90; H 3.78; N 4.48.

REFERENCE EXAMPLE 15

To a solution of ethyl 6-chloro-1,2-dihydro-2-oxo-4-phenyl-3-quinolinecarboxylate (3.27 g) in dichloromethane (30 ml) was added triethyloxonium fluoroborate (5.0 g), followed by stirring for 4 hours at room temperature. The mixture was washed with aqueous sodium hydrogen carbonate solution and water, dried ($MgSO_4$) and concentrated to remove the solvent. The oily residue was dissolved in ethanol (30 ml), to which potassium hydroxide (1.68 g) was added and refluxed for 3 hours. The mixture was diluted with water and adjusted to pH 2 by addition of 2N hydrochloric acid. The precipitated crystals were collected by filtration, thereby affording 6-chloro-2-ethoxy-4-phenyl-3-quinolinecarboxylic acid (2.48 g, 75.8%). Recrystallization from ethanol gave colorless prisms. mp 191°-192° C.

Elemental analysis for $C_{18}H_{14}ClNO_3$: Calculated : C 65.96; H 4.31; N 4.27; Found : C 65.92; H 4.31; N 4.21.

REFERENCE EXAMPLE 16

A mixture of ethyl 6-chloro-4-(2-chlorophenyl)-1,2-dihydro -2-oxo-3-quinolinecarboxylate (1.0 g), phosphorus oxychloride (5 ml) and pyridine (0.5 ml) was refluxed for 16 hours. The mixture was concentrated under reduced pressure. Water was added to the residue to obtain ethyl 2,6-dichloro-4-(2-chlorophenyl)-3-quinolinecarboxylate (0.7 g). The product was dissolved in methanol (20 ml), to which 28% sodium methoxide-methanol solution (0.5 ml) was added. The mixture was refluxed for 3 hours, and then diluted with water to obtain methyl 6-chloro-4-(2-chlorophenyl) -2-methoxy-3-quinolinecarboxylate as crystals (0.61 g, 61.0%). Recrystallization from methanol gave colorless needles. mp 151°-152° C.

Elemental analysis for $C_{18}H_{13}Cl_2NO_3$: Calculated : C 59.69; H 3.62; N 3.87; Found : C 59.91; H 3.61; N 3.87.

REFERENCE EXAMPLE 17

By the same method as in Reference Example 3, methyl 6-chloro-4-(2-chlorophenyl)-2-methoxy-3-quinolinecarboxylate was hydrolyzed to obtain 6-chloro-4-(2-chlorophenyl)-2-methoxy -3-quinolinecarboxylic acid as colorless prisms. Yield 76.3%. mp 188°-190° C.

Elemental analysis for $C_{17}H_{11}Cl_2NO_3$: Calculated : C 58.64; H 3.18; N 4.02; Found : C 58.43; H 3.07; N 4.13.

REFERENCE EXAMPLE 18

To a mixture of 2-amino-4,5,2'-trimethylbenzophenone (4.8 g), triethylamine (5.6 ml) and ethyl acetate (80 ml) was dropwise added methyl malonyl chloride (4.88 g) under ice-cooling and stirring. The mixture was stirred for an hour under ice-cooling, washed with water, dried ($MgSO_4$) and concentrated to remove the solvent. The oily product was dissolved in toluene (60 ml), and DBU (0.3 g) was added to the solution. The solution was refluxed for 30 minutes with removal of water using Dean-Stark's apparatus. The resulting solution was washed with diluted hydrochloric acid and water, dried ($MgSO_4$) and concentrated to obtain methyl 1,2-dihydro-6,7-dimethyl-4-(2-methylphenyl) -2-oxo-3-quinolinecarboxylate as crystals (5.3g, 82.6%). Recrystallization from ethanol - chloroform gave colorless needles. mp 288°-289° C.

Elemental analysis for $C_{20}H_{19}NO_3$: Calculated : C 74.75; H 5.96; N 4.36; Found : C 74.77; H 5.91; N 4.38.

REFERENCE EXAMPLE 19

Methyl 1,2-dihydro-6,7-dimethyl-4-(2-methylphenyl)-2-oxo-3-quinolinecarboxylate was methylated in the same way as in Reference Example 2 to obtain 1,2-dihydro-1,6,7-trimethyl -4-(2-methylphenyl)-2-oxo-3-quinolinecarboxylate. Yield 91.3% mp 170°-171° C. (from ethanol)

Elemental analysis for $C_{21}H_{21}NO_3$: Calculated : C 75.20; H 6.31; N 4.18; Found : C 75.20; H 6.38; N 4.11.

REFERENCE EXAMPLE 20

Methyl 1,2-dihydro-6,7-dimethyl-4-(2-methylphenyl)-2-oxo-3-quinolinecarboxylate was hydrolyzed in the same way as in Reference Example 3 to obtain 1,2-dihydro-6,7-dimethyl -4-(2-methylphenyl)-2-oxo-3-quinolinecarboxylic acid. Yield 97.4% mp 236°-237° C. (from acetone)

Elemental analysis for $C_{20}H_{19}NO_3$: Calculated : C 74.75; H 5.96; N 4.36; Found : C 74.82; H 6.00; N 4.31.

REFERENCE EXAMPLE 21

A mixture of 2-amino-3,,4,-dimethoxybenzophenone (4.07 g), diethyl malonate (4.8 g) and DBU (0.12 ml) was heated at 150°-160° C. for 2 hours. After cooling, the mixture was treated with ethanol to obtain ethyl 1,2-dihydro -4-(3,4-dimethoxyphenyl)-6-methyl-2-oxo-3-quinolinecarboxylate as crystals (5.0 g, 90.9%). Recrystallization from ethanol - chloroform gave colorless prisms. mp 220°-221° C.

Elemental analysis for $C_{21}H_{21}NO_5$: Calculated : C 68.65; H 5.76; N 3.81; Found : C 68.91; H 5.80; N 3.74.

REFERENCE EXAMPLE 22

Ethyl 1,2-dihydro-4-(3,4-dimethoxyphenyl)-6-methyl-2-oxo-3-quinolinecarboxylate was methylated in the same way as in Reference Example 2 to obtain ethyl 1,2-dihydro-4-(3,4-dimethoxyphenyl)-1,6-dimethyl-2-oxo-3-quinolinecarboxylate. Yield 85.6% mp 109°-110° C. (from 2-propanol)

Elemental analysis for $C_{22}H_{28}NO_5$: Calculated : C 69.28; H 6.08; N 3.63; Found : C 69.37; H 6.16; N 3.63.

REFERENCE EXAMPLE 23

Ethyl 1,2-dihydro-4-(3,4-dimethoxyphenyl)-6-methyl-2-oxo -3-quinolinecarboxylate was hydrolyzed in the same way as in Reference Example 3 to obtain 1,2-dihydro-4-(3,4-dimethoxyphenyl) -6-methyl-2-oxo-3-quinolinecarboxylic acid. Yield 86.9% mp 240°-241° C.(from ethanol - chloroform)

Elemental analysis for $C_{20}H_{19}NO_5$: Calculated : C 67.98; H 5.42; N 3.96; Found : C 68.03; H 5.45; N 3.97.

REFERENCE EXAMPLE 24

Ethyl 4-(2-chlorophenyl)-1,2-dihydro-6,8-dimethyl-2-oxo-3-quinolinecarboxylate was obtained by using the same method as in Reference Example 1. Yield 77.5% mp 257°-258° C. (from ethanol - chloroform)

Elemental analysis for $C_{20}H_{18}ClNO_3$: Calculated : C 67.51; H 5.10; N 3.94; Found : C 67.70; H 5.01; N 4.02.

REFERENCE EXAMPLE 25

To a mixture of ethyl 4-(2-chlorophenyl)-1,2-dihydro-6,8-dimethyl-2-oxo-3-quinolinecarboxylate (0.71 g), potassium carbonate (0.28 g) and DMF (8 ml) was dropwise added methyl iodide (0.15 ml) under stirring, followed by stirring for 15 minutes at room temperature. The mixture was poured into water and extracted with ethyl acetate. The organic layer was washed with water, dried ($MgSO_4$) and concentrated to obtain ethyl 4-(2-chlorophenyl)-2-methoxy-6,8-dimethyl-3-quinolinecarboxylate. Yield 90.3% mp 135°-136° C. (from ethanol)

Elemental analysis for $Cl_2H_{20}ClNO_3$: Calculated : C 68.20; H 5.45; N 3.79; Found : C 68.27; H 5.47; N 3.82.

REFERENCE EXAMPLE 26

Ethyl 4-(2-chlorophenyl)-2-methoxy-6,8-dimethyl-3-quinolinecarboxylate was hydrolyzed in the same way as in Reference Example 3 to obtain 4-(2-chlorophenyl)-2-methoxy-6,8-dimethyl-3-quinolinecarboxylic acid. Yield 78.4% mp 179°-180° C. (from isopropyl ether - hexane)

Elemental analysis for $C_{19}H_{16}ClNO_3$: Calculated : C 66.77; H 4.72; N 4.10; Found : C 66.96; H 4.82; N 4.05.

REFERENCE EXAMPLE 27

A mixture of 2-amino-2,-chloro-3,5-dimethylbenzophenone (2.6 g), methyl acetoacetate (2.32 g), conc. sulfuric acid (0.1 ml) and acetic acid (30 ml) was refluxed for 3 hours. The mixture was concentrated under reduced pressure, and the residue was made alkaline by addition of aqueous sodium hydrogen carbonate solution and extracted with ethyl acetate. The organic layer was washed with water, dried ($MgSO_4$) and distilled to remove the solvent. The residue was treated with isopropyl ether to obtain crystals of methyl 4-(2-chlorophenyl)-2,6,8-trimethyl-3-quinolinecarboxylate (2.53 g, 74.4%). The product was recrystallized from ethanol to give colorless prisms. mp 119°-120° C.

Elemental analysis for $C_{20}H_{18}ClNO_2$: Calculated : C 70.69; H 5.34; N 4.12; Found : C 70.67; H 5.37; N 4.08.

REFERENCE EXAMPLE 28

Methyl 4-(2-chlorophenyl)-2,6,8-trimethyl-3-quinolinecarboxylate was hydrolyzed by the same method as in Reference Example 28 to give 4-(2-chlorophenyl)-2,6,8-trimethyl-3-quinolinecarboxylic acid. Yield 89.1%. mp 278°-279° C.(from ethanol - chloroform)

Elemental analysis for $C_{19}H_{16}ClNO_2$: Calculated : C 70.05; H 4.95; N 4.30; Found : C 69.88; H 4.94; N 4.25.

REFERENCE EXAMPLE 29

Triethylamine (0.7 ml) was added dropwise to a mixture of 4-(2-chlorophenyl)-1,2-dihydro-1,6,7-trimethyl-2-oxo-3-quinolinecarboxylic acid (1.71 g), diphenylphosphoryl azide (1.65 g) and benzene (25 ml) under stirring. The mixture was further stirred for 15 minutes at room temperature and for 30 minutes under reflux, and then distilled to remove the solvent. The residue was dissolved in a mixture of dioxane (20 ml) and 1sodium hydroxide (7.5 ml) , followed by refluxing for 15 minutes. The resulting solution was acidified with 2N hydrochloric acid and then stirred for 20 minutes at room temperature. The mixture was made alkaline with 2N sodium hydroxide. The resultant crystals were collected by filtration to give 3-amino-4-(2-chlorophenyl)-1,6,7-trimethyl-2(1H)-quinolone (1.08 g, 69.2%), which was recrystallized from a mixture of chloroform and ethanol to give colorless needles. mp 242°-243° C.

Elemental analysis for $C_{18}H_{17}ClN_2O$: Calculated : C 69.12; H 5.48; N 8.96; Found : C 69.09; H 5.40; N 8.82.

REFERENCE EXAMPLE 30

Ethyl 4-(2-chlorophenyl)-1,2-dihydro-6-ethyl-2-oxo-3-quinolinecarboxylate was obtained by the same method as in Reference Example 21. Yield 95.0%. mp 199°-200° C. (from ethanol).

Elemental analysis for $C_{20}H_{18}ClNO_3$: Calculated : C 67.51; H 5.10; N 3.98; Found : C 67.25; H 5.20; N 3.92.

REFERENCE EXAMPLE 31

By the same method as in Reference Example 2, ethyl 4-(2-chlorophenyl)-1,2-dihydro-6-ethyl-2-oxo-3-quinolinecarboxylate was methylated to give ethyl 4-(2-chlorophenyl)-1,2-dihydro-6-ethyl-1-methyl-2-oxo-3-quinolinecarboxylate. Yield 96.2%. mp 125°-126° C. (from ethanol hexane)

Elemental analysis for $C_{21}H_{20}ClNO_3$: Calculated : C 68.20; H 5.45; N 3.79; Found : C 68.20; H 5.42; N 3.78.

REFERENCE EXAMPLE 32

Ethyl 4-(2-chlorophenyl)-1,2-dihydro-6-ethyl-1-methyl-2-oxo-3-quinolinecarboxylate was hydrolyzed by the method as in Reference Example 3 to give 4-(2-chlorophenyl)-1,2-dihydro-6-ethyl-1-methyl-2-oxo-3-quinolinecarboxylic acid. Yield 94.4%. mp 200°-201° C. (from ethanol)

Elemental analysis for $C_{19}H_{16}ClNO_3$: Calculated : C 66.77; H 4.72; N 4.10; Found : C 66.84; H 4.75; N 4.07.

REFERENCE EXAMPLE 33

Ethyl 4-(2-chlorophenyl)-1,2-dihydro-6-isopropyl-2-oxo-3-quinolinecarboxylate was obtained by the same method as in Reference Example 21. Yield 63.0%. mp 173°-174° C. (from ethanol - hexane).

Elemental analysis for $C_{21}H_{20}ClNO_3$: Calculated : C 68.20; H 5.45; N 3.79; Found : C 68.37; H 5.51; N 3.82.

REFERENCE EXAMPLE 34

Ethyl 4-(2-chlorophenyl)-1,2-dihydro-6-isopropyl-2-oxo-3-quinolinecarboxylate was methylated by the same method as in Reference Example 2 to give ethyl 4-(2chlorophenyl)-1,2-dihydro-6-isopropyl-1-methyl-2-oxo-3-quinolinecarboxylate. Yield 65.7%. mp 140°-142° C. (from ethanol)

Elemental analysis for $C_{22}H_{22}ClNO_3$: Calculated : C 68.84; H 5.78; N 3.65; Found : C 68.96; H 5.78; N 3.65.

REFERENCE EXAMPLE 35

Ethyl 4-(2-chlorophenyl)-1,2-dihydro-6-isopropyl-1-methyl-2-oxo-3-quinolinecarboxylate was obtained was hydrolyzed by the same method as in Reference Example 3 to give 4-(2-chlorophenyl)-1,2-dihydro-6-isopropyl-1-methyl-2-oxo-3-quinolinecarboxylic acid. Yield 88.5%. mp 184°-185° C. (from ethanol)

Elemental analysis for $C_{20}H_{18}ClNO_3$: Calculated : C 67.51; H 5.10; N 3.94; Found : C 67.49; H 5.07; N 3.94.

REFERENCE EXAMPLE 36

Ethyl 6-chloro-1,2-dihydro-4-(2-methylphenyl)-2-oxo-3-quinolinecarboxylate was obtained by the same method as in Reference Example 21. Yield 84.2% mp 215°–216° C. (from ethanol)

Elemental analysis for $C_{19}H_{16}ClNO_3$: Calculated : C 66.77; H 4.72; N 4.10; Found : C 66.84; H 4.47; N 4.14.

REFERENCE EXAMPLE 37

Ethyl 6-chloro-1,2-dihydro-4-(2-methylphenyl)-2-oxo-3-quinolinecarboxylate was methylated by the same method as in Reference Example 2 to give ethyl 6-chloro-1,2-dihydro -1-methyl-4-(2-methylphenyl)-2-oxo-3-quinolinecarboxylate. Yield 88.5% mp 113°–114° C. (from ethanol)

Elemental analysis for $C_{20}H_{18}ClNO_3$: Calculated : C 67.51; H 5.10; N 3.94; Found : C 67.60; H 5.17; N 3.90.

REFERENCE EXAMPLE 38

Ethyl 6-chloro-1,2-dihydro-1-methyl-4-(2-methylphenyl) -2-oxo-3-quinolinecarboxylate was hydrolyzed by the same method as in Reference Example 3 to give 6-chloro-1,2-dihydro-1-methyl-4-(2-methylphenyl)-2-oxo-3-quinolinecarboxylic acid. Yield 88.2%. mp 202°–203° C. (from Elemental analysis for $C_{18}H_{14}ClNO_3$: Calculated : C 65.96; H 4.31; N 4.27; Found : C 65.91; H 4.38; N 4.24.

REFERENCE EXAMPLE 39

Ethyl 6-chloro-1,2-dihydro-4-(3,4-dimethoxyphenyl)-2-oxo -3-quinolinecarboxylate was obtained by the same method as in Reference Example 21. Yield 76.8%. mp 209°–210° C. (from ethanol)

Elemental analysis for $C_{20}H_{18}ClNO_5$: Calculated : C 61.94; H 4.68; N 3.61; Found : C 61.77; H 4.65; N 3.58.

REFERENCE EXAMPLE 40

Ethyl 6-chloro-1,2-dihydro-4-(3,4-dimethoxyphenyl)-2-oxo -3-quinolinecarboxylate was methylated by the same method as in Reference Example 2 to give ethyl 6-chloro-1,2-dihydro-1-methyl-4-(3,4-dimethoxyphenyl)-2-oxo-3quinolinecarboxylate. Yield 99.6%. mp 104°–106° C. (from ethanol)

Elemental analysis for $C_{21}H_{20}ClNO_5$: Calculated : C 62.77; H 5.02; N 3.49; Found : C 62.88; H 5.01; N 3.43.

REFERENCE EXAMPLE 41

Ethyl 6-chloro-1,2-dihydro-1-methyl-4-(3,4-dimethoxyphenyl) -2-oxo-3-quinolinecarboxylate was hydrolyzed by the same method as in Reference Example 3 to give 6-chloro-1,2-dihydro-1-methyl-4-(3,4-dimethoxyphenyl)-2-oxo-3 quinolinecarboxylic acid. Yield 93.0%. mp 230°–232° C. (from ethanol - chloroform)

Elemental analysis for $C_{19}H_{16}ClNO_5$: Calculated : C 61.05; H 4.31; N 3.75; Found : C 61.00; H 4.24; N 3.79.

REFERENCE EXAMPLE 42

Ethyl 7-chloro-1,2-dihydro-6-methyl-4-(2-methylphenyl) -2-oxo-3-quinolinecarboxylate was obtained by the same method as in Reference Example 21. Yield 93.8%. mp 290°–291° C. (from ethanol - chloroform)

Elemental analysis for $C_{20}H_{18}ClNO_3$: Calculated : C 67.51; H 5.10; N 3.94; Found : C 67.82; H 5.17; N 3.92.

REFERENCE EXAMPLE 43

Ethyl 7-chloro-1,2-dihydro-6-methyl-4-(2-methylphenyl) -2-oxo-3-quinolinecarboxylate was methylated by the same method as in Reference Example 2 to give ethyl 7-chloro -1,2-dihydro-1,6-dimethyl-4-(2-methylphenyl)-2-oxo-3-quinoline-carboxylate. Yield 89.7%. mp 121°–123° C. (from ethanol - chloroform)

Elemental analysis for $C_{21}H_{20}ClNO_3$: Calculated : C 68.20; H 5.45; N 3.79; Found : C 68.32; H 5.46; N 3.77.

REFERENCE EXAMPLE 44

Ethyl 7-chloro-1,2-dihydro-1,6-dimethyl-4-(2-methylphenyl) -2-oxo-3-quinolinecarboxylate was hydrolyzed by the same method as in Reference Example 3 to give 7-chloro-1,2-dihydro-1,6-dimethyl-4-(2-methylphenyl)-2-oxo-3quinoline carboxylic acid. Yield 97.8%. mp 204°–205° C. (from ethanol)

Elemental analysis for $C_{19}H_{16}ClNO_3$: Calculated : C 66.77; H 4.72; N 4.10; Found : C 66.82; H 4.71; N 4.09.

We claim:

1. A quinoline derivative of the formula (I):

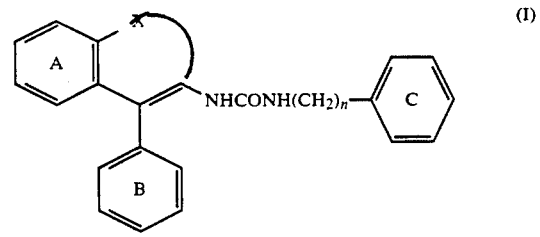

wherein the ring A has one or two lower alkyl or halogen substituents, the ring B has one halogen or lower alkyl substituent or two lower alkoxy substituents, and the ring C has two halogen substituents or the same or different two lower alkyl substituents, X is

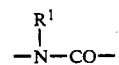

wherein $R^1$ is a hydrogen atom or a lower alkyl group or

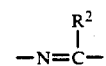

wherein $R^2$ is a lower alkyl group or a lower alkoxy group, and n is 0 or 1, or its salt.

2. A compound of claim 1 in which n is 0 and X is

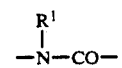

wherein $R^1$ is a lower alkyl group.

3. A compound of claim 1 in which n is 0 and X is

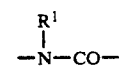

wherein $R^1$ is a lower alkyl group.

4. A compound of claim 1 in which n is 0 and X is $$\begin{array}{c} R^1 \\ | \\ -N-CO- \end{array}$$

wherein R¹ is methyl, the ring A has one or two methyl or ethyl, isopropyl or chlorine substituents, the ring B has chlorine or methyl substituents or two methoxy substituents, and the ring C has two fluorine substituents or isopropy and methyl substituents.

5. A method of inhibiting acyl-CoA : cholesterol acyltransferase which comprises administering to a patient in need thereof an effective amount of a compound according to claim 1.

6. An acyl-CoA : cholesterol acyltransferase inhibitory composition comprising a pharmaceutically effective amount of a quinoline derivative of the formula (I):

(I)

wherein the ring A has one or two lower alkyl or halogen substituents, the ring B has one halogen or lower alkyl substituent or two lower alkoxy substituents, and the ring C has two halogen substituents or the same or different two lower alkyl substituents, X is $$\begin{array}{c} R^1 \\ | \\ -N-CO- \end{array}$$

wherein R¹ is a hydrogen atom or a lower alkyl group or $$\begin{array}{c} R^2 \\ | \\ -N=C- \end{array}$$

wherein R² is a lower alkyl group or a lower alkoxy group, and n is 0 or 1, or its pharmaceutically acceptable salt and a pharmaceutically acceptable carrier, diluent or excipient.

7. A composition of claim 6 in which n is 0 and X is $$\begin{array}{c} R^2 \\ | \\ -N=C- \end{array}$$

wherein R¹ is a lower alkyl group.

8. A composition of claim 6 in which n is 0 and X is $$\begin{array}{c} R^2 \\ | \\ -N=C- \end{array}$$

wherein R¹ is methyl, the ring A has one or two methyl or ethyl, isopropyl or chlorine substituents, the ring B has chlorine or methyl substituents or two methoxy substituents, and the ring C has two fluorine substituents or isopropyl and methyl substituents.

9. A compound of claim 1 of the formula N-[4-(2-chlorophenyl)-1,6,7-trimethyl-1,2-dihydro-2-oxo-3-quinolyn]-N'-(2,4-difluorophenyl) urea or its salt.

10. A compound of claim 1 of the formula N-[4-(2-chlorophenyl)-1-ethyl-1,2-dihydro-6,8-dimethyl-2-oxo-3-quinolyn]-N'-(2,4-difluorophenyl) urea or its salt.

11. A compound of claim 1 of the formula N-(2,4-difluorophenyl)-N'-(1,2-dihydro-1,6,7-trimethyl-4-(2-methylphenyl) -2-oxo-3-quinolyl]urea or its salt.

12. A compound of claim 1 of the formula N-(2,4-difluorophenyl)-N'-[1,2-dihydro-4-(3,4-di-methoxyphenyl)-1,6-dimethyl-2-oxo-3-quinolyl]urea or its salt.

13. A compound of claim 1 of the formula N-[(4-(2-chlorophenyl)-1,2-dihydro-6-ethyl-1-methy-1-2-oxo-3-quinolyl]-N'-(2,4-difluorophenyl)urea or its salt.

14. A compound of claim 1 of the formula N-[4-(2-chlorophenyl)-1,2-dihydro-6-ethyl-1-methyl-2-oxo-3-quinolyl]-N'-(2-isopropyl-6-methylphenyl)urea or its salt.

15. A compound of claim 1 of the formula N-[6-chloro-1,2-dihydro-1-methyl-4-(2-methylphenyl)-2-oxo-3-quinolyl]-N'-(2-isopropyl-6-methylphenyl)urea or its salt.

16. A compound of claim 1 of the formula N-[7-chloro-1,2-dihydro-4-(2-methylphenyl)-1,6-dimethyl-2-oxo-3-quinolyl]-N'-(2,4-difluorophenyl)urea, or its salt.

17. A method of inhibiting acyl-Co : cholesterol acyltransferase which comprises administering to a patient in need thereof an effective amount of the compound of claim 9.

18. A method of inhibiting acyl-Co : cholesterol acyltransferase which comprises administering to a patient in need thereof an effective amount of the compound of claim 10.

19. A method of inhibiting acyl-Co : cholesterol acyltransferase which comprises administering to a patient in need thereof an effective amount of the compound of claim 1.

20. A method of inhibiting acyl-Co : cholesterol acyltransferase which comprises administering to a patient in need thereof an effective amount of the compound of claim 12.

21. A method of inhibiting acyl-Co : cholesterol acyltransferase which comprises administering to a patient in need thereof an effective amount of the compound of claim 13.

22. A method of inhibiting acyl-Co : cholesterol acyltransferase which comprises administering to a patient in need thereof an effective amount of the compound of claim 14.

23. A method of inhibiting acyl-Co : cholesterol acyltransferase which comprises administering to a patient in need thereof an effective amount of the compound of claim 15.

24. A method of inhibiting acyl-Co : cholesterol acyltransferase which comprises administering to a patient in need thereof an effective amount of the compound of claim 16.

* * * * *